United States Patent [19]

Nardone, Jr

[11] Patent Number: 5,285,530
[45] Date of Patent: Feb. 15, 1994

[54] EAR MUFF DEVICE

[76] Inventor: Robert J. Nardone, Jr, 2717 Burwell St., Union, N.J. 07083

[21] Appl. No.: 12,770

[22] Filed: Feb. 3, 1993

[51] Int. Cl.$^5$ .............................................. A61F 11/14
[52] U.S. Cl. ..................................... 2/209; 2/DIG. 11
[58] Field of Search .................. 2/209, 423, DIG. 11, 2/208, 209.1, 171; 472/70, 133; 40/329, 586; 273/DIG. 17; D2/263

[56] References Cited

U.S. PATENT DOCUMENTS

| | | | |
|---|---|---|---|
| D. 279,141 | 6/1985 | Poland | D2/385 |
| 4,724,548 | 2/1988 | London | 2/338 |
| 4,814,632 | 3/1989 | Glaeser et al. | 2/160 |
| 5,052,194 | 10/1991 | Jarus | 2/209 |

Primary Examiner—Clifford D. Crowder
Assistant Examiner—Amy B. Vanatta
Attorney, Agent, or Firm—Leon Gilden

[57] ABSTRACT

An ear muff device is arranged to include a resilient band, with the band of a generally semi-circular configuration of resilient construction, including a glove-shaped member at each end thereof, wherein each glove-shaped member is arranged to receive an ear of an individual in surrounding relationship relative to the ear to impart warmth to the ear in use. A modification of the invention includes audio conduit structure directed through the glove members to direct and ease audio hearing of an individual in use of the organization.

3 Claims, 5 Drawing Sheets

EAR MUFF DEVICE

BACKGROUND OF THE INVENTION

1. Field of the Invention

The field of the invention relates to ear muff structure, and more particularly pertains to a new and improved ear muff device wherein the same is arranged to receive and direct warmth to an individual's ears in use.

2. Description of the Prior Art

Ear muff structure of various types have been utilized throughout the prior art and exemplified by the U.S. Pat. Nos. 4,850,055 and 4,935,965. U.S. Pat. Nos. 313,092; 288,141; and 254,876 are further examples of ear muff construction configurations.

The instant invention attempts to overcome deficiencies of the prior art by providing for a glove structure arranged to receive and envelope the ear and additionally and optionally include audio conduit structure arranged to ease hearing through the glove members and in this respect, the present invention substantially fulfills this need.

SUMMARY OF THE INVENTION

In view of the foregoing disadvantages inherent in the known types of ear muff structure now present in the prior art, the present invention provides an ear muff device wherein the same is arranged to receive and insulate the ear members of an individual in use. As such, the general purpose of the present invention, which will be described subsequently in greater detail, is to provide a new and improved ear muff device which has all the advantages of the prior art ear muff structure and none of the disadvantages.

To attain this, the present invention provides an ear muff device arranged to include a resilient band, with the band of a generally semi-circular configuration of resilient construction, including a glove-shaped member at each end thereof, wherein each glove-shaped member is arranged to receive an ear of an individual in surrounding relationship relative to the ear to impart warmth to the ear in use. A modification of the invention includes audio conduit structure directed through the glove members to direct and ease audio hearing of an individual in use of the organization.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved ear muff device which has all the advantages of the prior art ear muff structure and none of the disadvantages.

It is another object of the present invention to provide a new and improved ear muff device which may be easily and efficiently manufactured and marketed.

It is a further object of the present invention to provide a new and improved ear muff device which is of a durable and reliable construction.

An even further object of the present invention is to provide a new and improved ear muff device which is susceptible of a low cost of manufacture with regard to both materials and labor, and which accordingly is then susceptible of low prices of sale to the consuming public, thereby making such ear muff devices economically available to the buying public.

Still yet another object of the present invention is to provide a new and improved ear muff device which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 2:
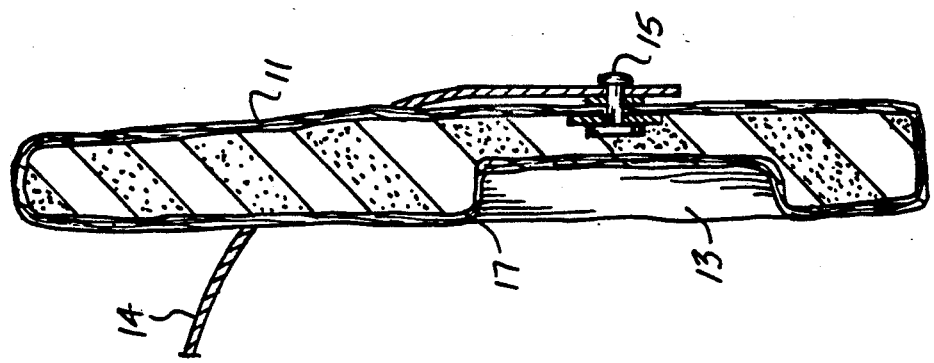
FIG. 2 is an orthographic view, taken along the lines 2—2 of FIG. 1 in the direction indicated by the arrows.

With reference now to the drawings, and in particular to FIGS. 1 to 10 thereof, a new and improved ear muff device embodying the principles and concepts of the present invention and generally designated by the reference numerals 10, 10a, and 10b will be described.

Figure 1:
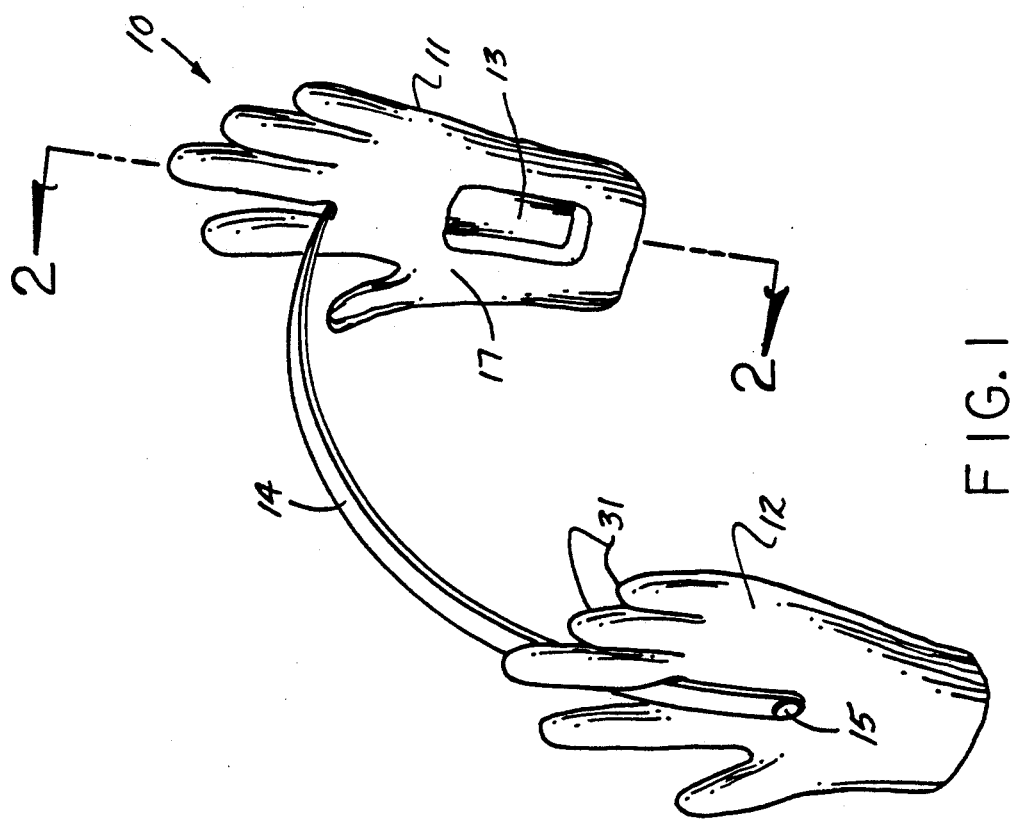
FIG. 1 is an isometric illustration of the invention.
Figure 3:
FIG. 3 is an isometric illustration of the invention in use.

More specifically, the ear muff device 10 of the instant invention essentially comprises a plurality of glove members 11 of identical and mirror image construction, having a palm portion 17 and a plurality of glove fingers 31, with each glove member including a facing first side and an exterior second side opposed to a respective first side. The structure as indicated in FIG. 1 is arranged to include a recess 13 directed into each palm portion 17 to receive an ear of an individual to engage and insulate the ear in use of the organization. A resilient band 14 of a shape retentive material and of a generally semi-annular configuration has each end pivotally mounted about a band anchor 15 to an exterior surface of each of the glove member 11.

Figure 4:
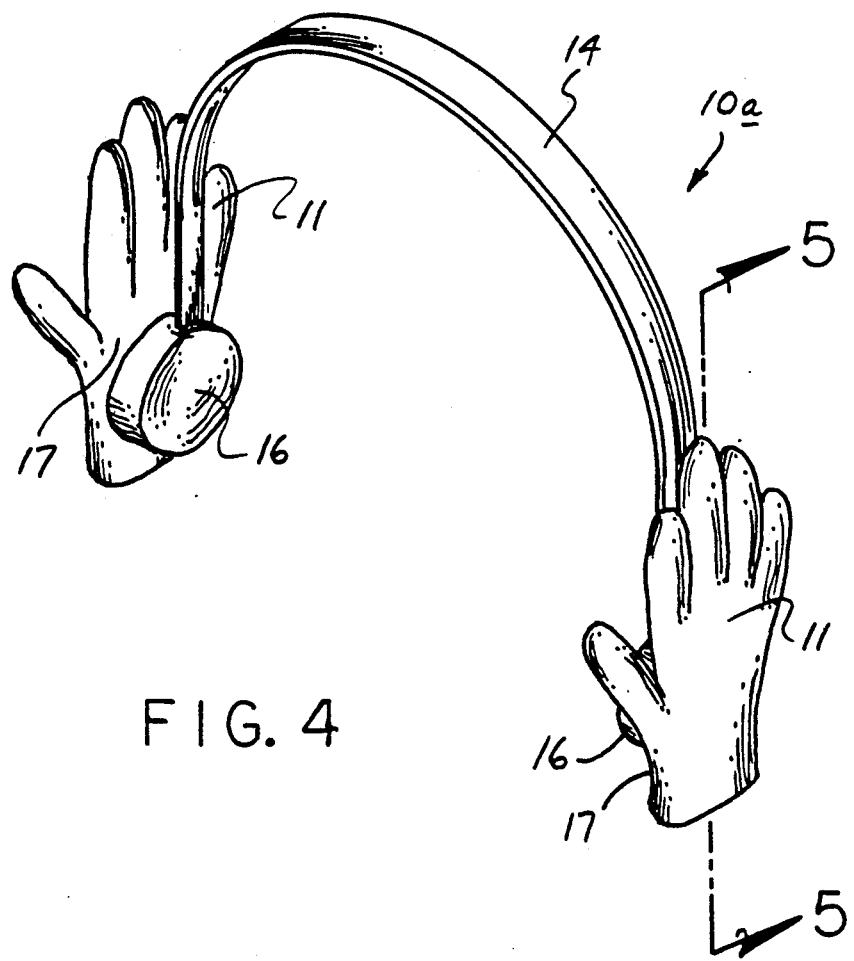
FIG. 4 is an isometric illustration of a modified aspect of the invention.
Figure 5:
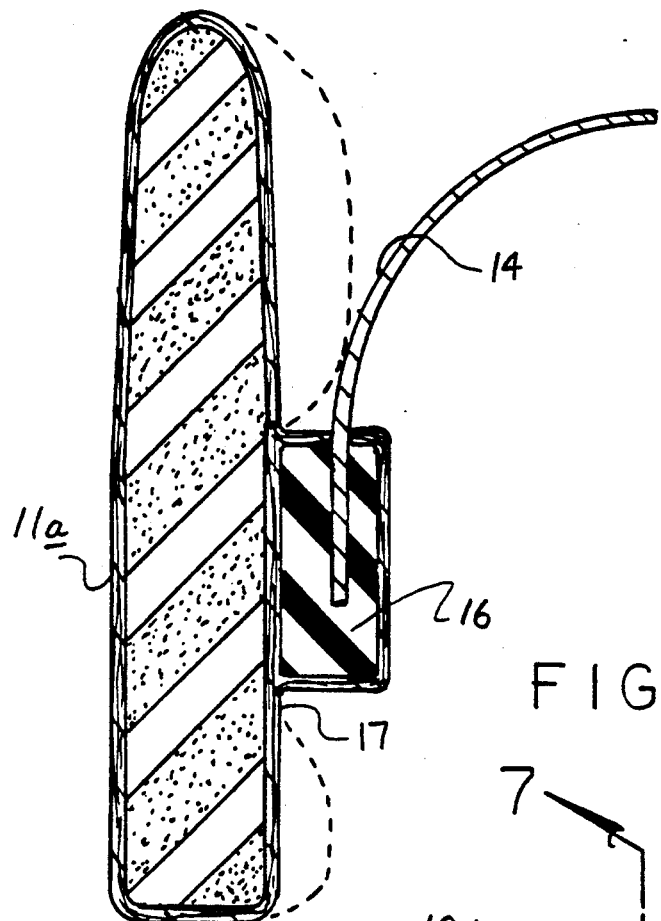
FIG. 5 is an orthographic view, taken along the lines 5—5 of FIG. 4 in the direction indicated by the arrows.
Figure 6:
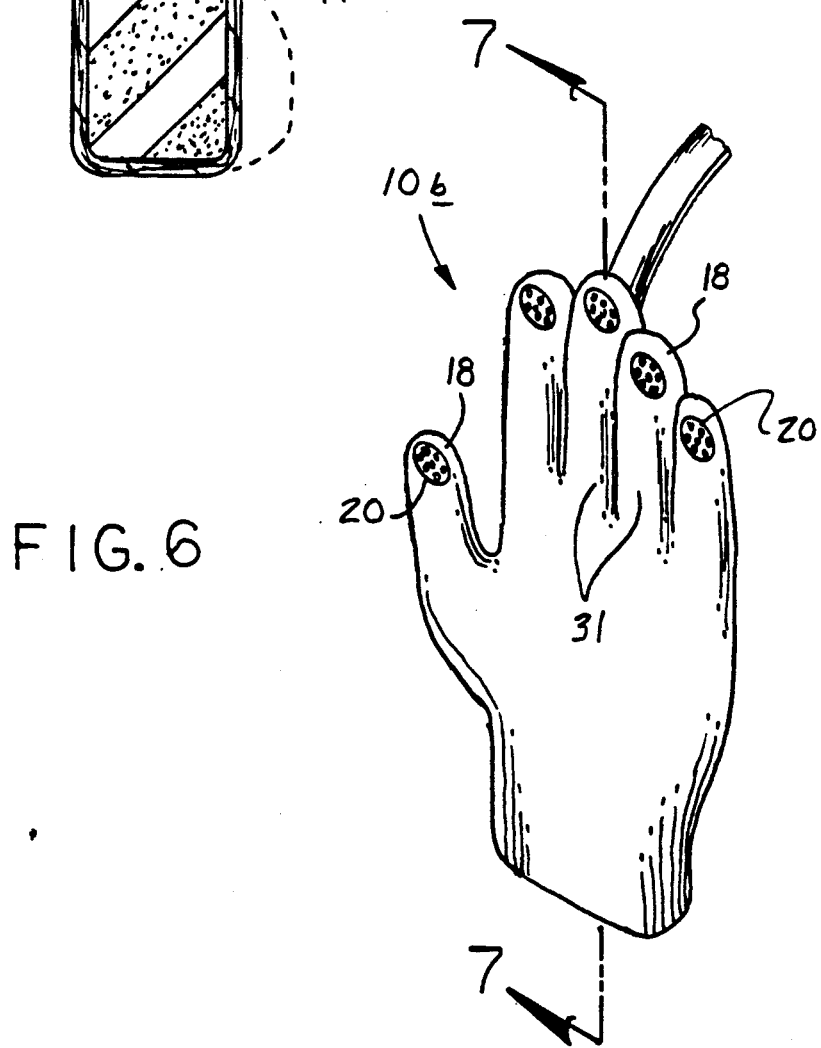
FIG. 6 is an isometric illustration of a further modified aspect of the glove structure of the invention.
Figure 7:
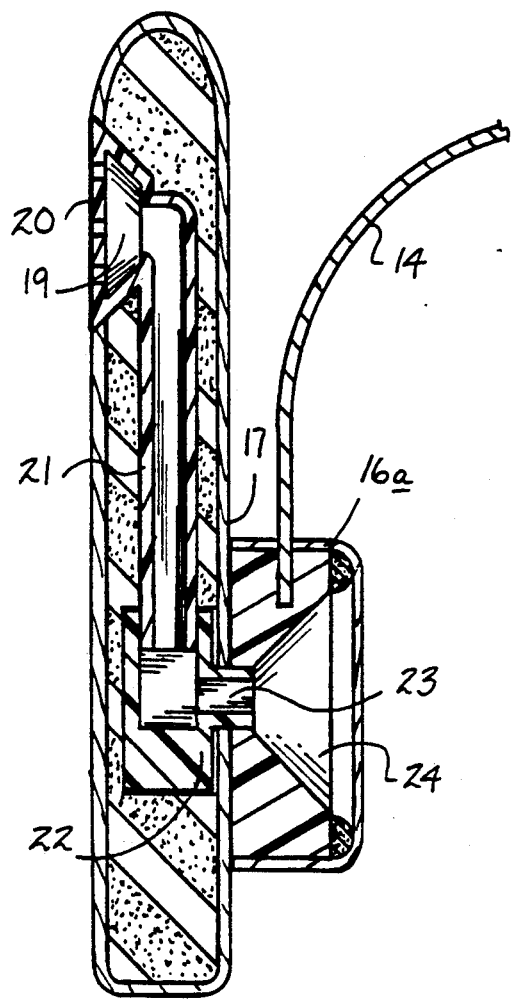
FIG. 7 is an orthographic view, taken along the lines 7—7 of FIG. 6 in the direction indicated by the arrows.
Figure 8:
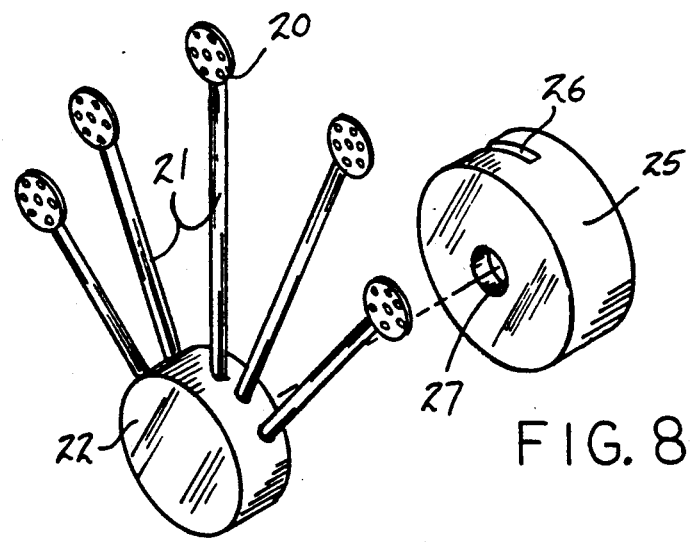
FIG. 8 is an isometric exploded view of the audio conduit structure arranged for mounting to a support housing.
Figure 9:
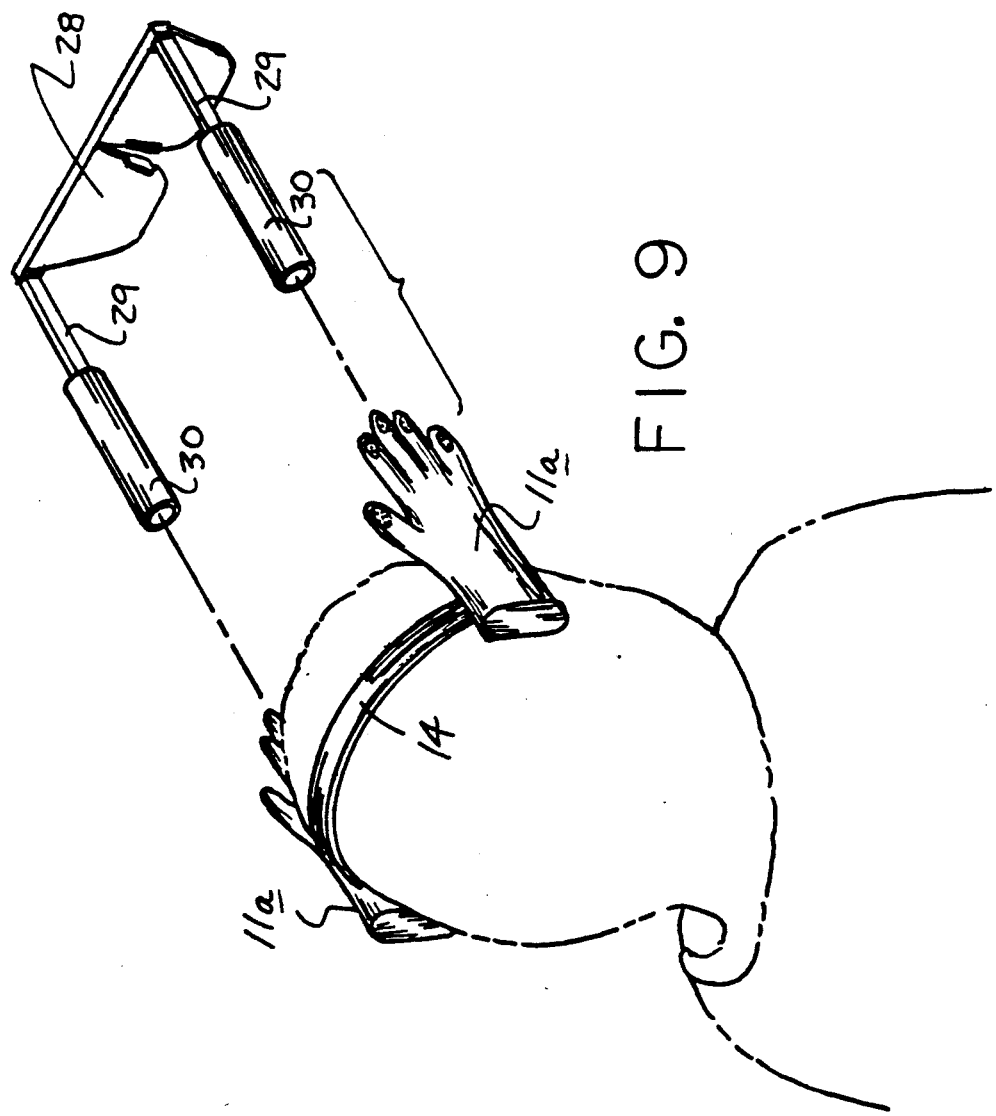
FIG. 9 is an isometric illustration of the invention employing the support housing permitting rotation of the glove members to receive an eyeglass structure.
Figure 10:
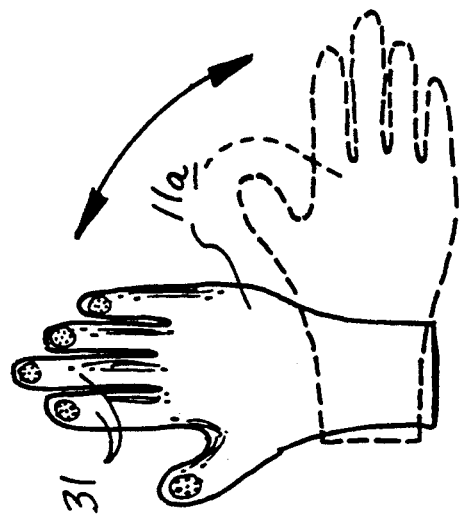
FIG. 10 is an orthographic side view of the glove members arranged for pivoting orientation as employed in FIG. 9.

The device 10a, as indicated in the FIGS. 4 and 5, includes a boss pad 16 projecting from each first side of a modified glove member 11a, wherein the glove members 11a in the construction of the FIGS. 4–10 is formed of a resilient material arranged to deform in a surrounding relationship about each of the boss pads 16 to surround an ear portion and provide insulative warmth thereto. The device 10b, as indicated in the FIGS. 7–10 has each of the finger members 31, including a finger tip 18, having a conical entrance opening 19 projecting through the finger tip 18 to an exterior side of each associated glove 11a. An apertured cover web 20 is positioned in a coplanar relationship relative to the glove member's exterior surface to prevent undesirable debris from entering the entrance opening 19. An audio conduit 21 of a flexible construction permitting deflection of the glove 11a, in a manner as indicated in FIG. 5, is provided and is directed in audio communication between the entrance opening 19 and a manifold boss 22 that directs audio communication between the first conduit 21 and audio second conduit 23 orthogonally oriented relative to the first conduit 21. The audio second conduit 23 is directed into a conical exit port 24 within the modified boss pad 16a, wherein the manifold boss 22 is mounted within the glove 11a in adjacency to the palm 17. Each modified boss pad 16a is pivotally mounted within a boss pad cylindrical support housing 25, having a cylindrical side wall to include a cylindrical side wall slot 26 to slidably receive an end portion of the resilient band 14 to permit pivoting of the band relative to the support housing 25. To this end, each second conduit 23 is pivotally mounted relative to the boss pad 16a to permit its pivoting in conjunction with the band 14 relative to the support housing 25, that in turn is arranged in a fixed orientation relative to the palm 17. Rotative pivoting of the glove members 11a is thereby permitted, in a manner as indicated in FIG. 9, with one of each finger 31 of a respective glove 11a arranged to receive a resilient tube 30, that in turn is mounted to an associated frame leg 29 of an eyeglass member set 28. In this manner, an individual may secure their eyeglasses onto the glove members for novelty or for permitting prescription lenses to be readily employed in use of the ear muff structure of the invention.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An ear muff device, comprising,
   a plurality of glove members, the glove members of a mirror image construction, each glove member having an interior surface and an exterior surface, each glove member including a plurality of glove fingers, and each glove member having a glove palm, with each glove palm arranged in a facing relationship,
   and
   a resilient band pivotally mounted to the glove members, wherein the resilient band is of a shape-retentive material, and having a semi-annular configuration, and
   each palm includes a boss pad to provide a plurality of boss pads with the resilient band mounted to the boss pads, and each glove member mounted in resilient surrounding relationship to one of said boss pads to impart a surrounding relationship of each glove member relative to said one of said boss pad.

2. An ear muff device as set forth in claim 1 wherein each of the glove fingers includes a conical entrance opening within each glove finger, and each entrance opening having an apertured cover web substantially coplanar with said exterior surface of one of said glove members, and each entrance opening having an audio first conduit directed through one of said glove fingers, and each audio first conduit received within a manifold boss, with the manifold boss mounted within the glove member in adjacency to the boss pad, and the manifold boss having a second conduit directed from the manifold boss through the glove palm, with the second conduit rotatably mounted to the manifold boss, and the second conduit having a conical exit port, with the conical exit port mounted within the boss pad.

3. An ear muff device as set forth in claim 2 including a cylindrical support housing pivotally mounted about each boss pad, with each cylindrical support housing having a cylindrical side wall, with the cylindrical side wall including a side wall slot to receive the resilient band, with each housing mounted fixedly to one of said glove members permitting pivoting of the glove members relative to the band, and an eyeglass member set, wherein the eyeglass member set includes a plurality of frame legs, and each frame leg including a resilient tube, and each resilient tube arranged for reception about one of the glove fingers of one of the glove members.

* * * * *